United States Patent
Milius et al.

(10) Patent No.: US 6,464,993 B1
(45) Date of Patent: Oct. 15, 2002

(54) USE OF A COMPOSITION BASES ON ISOSTEARYL GLYCOSIDE AND ISOSTEARYL ALCOHOL AS AN AGENT THAT IMPROVES THE RESISTANCE OF A COSMETIC COMPOSITION TO WATER

(75) Inventors: Alain Milius, Nice; Nelly Michel, Maisons Alfort; Bernard Branco, Le Chesnay; Jean-Pierre Boiteux, Castres; Chantal Almaric, Blan; Alicia Roso, Saix, all of (FR)

(73) Assignee: Societe d'Exploitation de Produits pour les Industries Chimiques-Seppic, Paris (FR)

( * ) Notice: Subject to any disclaimer, the term of this patent is extended or adjusted under 35 U.S.C. 154(b) by 0 days.

(21) Appl. No.: 09/937,733

(22) PCT Filed: Mar. 29, 2000

(86) PCT No.: PCT/FR00/00777

§ 371 (c)(1),
(2), (4) Date: Sep. 27, 2001

(87) PCT Pub. No.: WO00/59455

PCT Pub. Date: Oct. 12, 2000

(30) Foreign Application Priority Data

Mar. 30, 1999 (FR) ............................................. 99 03951

(51) Int. Cl.$^7$ ............................. A61K 7/00; C07G 3/00
(52) U.S. Cl. ........................ 424/401; 424/400; 514/724; 514/937; 514/938; 514/939; 536/4.1; 536/18.6
(58) Field of Search ................................. 424/400, 401; 514/724, 937, 938, 939; 536/4.1, 18.6

(56) References Cited

U.S. PATENT DOCUMENTS 5,631,357 A * 5/1997 Weuthen et al. ........... 536/18.6
5,795,978 A * 8/1998 Ansmann et al. ........... 536/120

\* cited by examiner

*Primary Examiner*—Shelley A. Dodson
(74) *Attorney, Agent, or Firm*—Timothy J. Keefer; Wildman, Harrold, Allen & Dixon

(57) ABSTRACT

The present invention relates to the use of a composition comprising:

- 10 to 90% by weight, preferably 10 to 50% by weight and particularly preferably 10 to 40% by weight of an isostearyl glycoside with a degree of polymerization of between 1 and 3; and
- 90 to 10% by weight, preferably 90 to 50% by weight and particularly preferably 90 to 60% by weight of isostearyl alcohol as an agent for improving the water resistance of a cosmetic composition.

13 Claims, No Drawings

USE OF A COMPOSITION BASES ON ISOSTEARYL GLYCOSIDE AND ISOSTEARYL ALCOHOL AS AN AGENT THAT IMPROVES THE RESISTANCE OF A COSMETIC COMPOSITION TO WATER

The present invention relates essentially to the use of compositions based on isostearyl glycoside and isostearyl alcohol for the manufacture of cosmetic compositions with improved water resistance.

It is known that cosmetic compositions in the form especially of oil-in-water, water-in-oil or water-in-oil-in-water emulsions have a relatively inadequate water resistance.

It has been found for example that the efficacy of sun formulations, mascaras or baby care products decreases considerably after they have come into contact with water.

Different solutions have been proposed in the state of the art for overcoming this disadvantage and prolonging the action of such compositions over time.

Thus a first means of increasing the water resistance of cosmetic compositions consists in the incorporation, in a dose generally of between 1 and 5%, of various hydrophobic polymers and more particularly of vinylic copolymers such as the products marketed under the names ANTARON® or GANEX®; high-molecular acrylic copolymers, for example the product marketed under the name DERMACRYL® LT,79 by NATIONAL STARCH; or polymers of vegetable origin such as the product marketed under the name GLOSSAMER® by TRI-K.

The polymers and copolymers used in this way as agents for improving the water resistance of cosmetic compositions are generally in the form of a paste or solid, so these products are relatively difficult to handle and necessarily have to be incorporated into a phase preheated to 80° C.

Thus the ANTARON® products have to be melted and introduced into the fatty phase, with agitation, until they have dissolved, before they can be incorporated into the rest of the emulsion. Also, they have to be used under very precise HLB (hydrophilic-lipophilic balance) conditions and preferably in the presence of anionic emulsifiers.

Furthermore, the products of the DERMACRYL® type have to be at least 80% neutralized with an appropriate amount of base and have to be added slowly, with agitation. They can also be introduced into cosmetic compositions without prior neutralization, but it is then necessary to solubilize them either in alcohols or in ethanol.

Consequently, it is apparent that the use of polymers and copolymers as agents for improving the water resistance of cosmetic compositions creates practical difficulties which have limited their value.

A second means of improving the water resistance of cosmetic compositions consists in the incorporation of substantial amounts (greater than 40% by weight) of fatty phase containing conventional mineral oils and silicone phases such as silicone gums and particularly high-molecular polydimethylsiloxanes (cyclomethiconel dimethiconol), silicone resins (dimethicone/trimethylsiloxy silicate) or products of the phenyltrimethicone type.

The incorporation of such amounts of fatty phase presents difficult problems as regards the stabilization, particularly temperature stabilization, of the emulsions prepared. Oil exudation phenomena are also observed over time and these are unacceptable where cosmetic applications are concerned.

Also, the use of such amounts of fatty phases considerably increases the cost of these emulsions.

In general terms, all the means which have so far been envisaged in the state of the art for improving the water resistance of cosmetic compositions have produced emulsions which are difficult to spread and have a greasy and sticky feel.

Under these conditions, the object of the present invention is to solve the technical problem which consists in the provision of novel cosmetic compositions with improved water resistance which can be obtained relatively easily and inexpensively, are easy to spread and have a pleasant feel.

It has been discovered that the above-mentioned technical problem can be solved by the use of certain compositions based on isostearyl glycoside and isostearyl alcohol as agents for improving the water resistance of a variety of cosmetic compositions; it is this discovery which forms the basis of the present invention.

Thus, according to a first feature, the present invention relates to the use of a composition comprising 10 to 90% by weight, preferably 10 to 50% by weight and particularly preferably 10 to 40% by weight of an isostearyl glycoside with a degree of polymerization of between 1 and 3, and 90 to 10% by weight, preferably 90 to 50% by weight and particularly preferably 90 to 60% by weight of isostearyl alcohol, as an agent for improving the water resistance of a cosmetic composition.

The originality of the present invention compared with the prior art is that it makes it possible to obtain cosmetic compositions with improved water resistance without detracting from either the spreadability or the sensory properties (light feel, non-sticky character) of these compositions.

The compositions based on isostearyl glycoside and isostearyl alcohol which are used within the framework of the present invention are generally in liquid form. They are thus particularly easy to use and their application does not require any special precautions. In particular, these compositions can be applied cold and without additional stabilizer.

Within the framework of the present description, the expression "isostearyl glycoside with a degree of polymerization of between 1 and 3" is understood as denoting compounds of the formula $$RO(G)_x$$

in which:

R is an isostearyl radical;

x is a number between 1 and 3; and

G is a reducing glycopyranose or glycofuranose residue and preferably a glucose residue.

Advantageously, the degree of polymerization represented by x is between 1.05 and 2.5 and preferably between 1.1 and 2.

The isostearyl glycosides used within the framework of the present invention are not always pure.

In fact, they can also contain minor proportions of compounds of the same type in which the alkyl radicals have a longer and/or shorter chain, such compounds being derived especially from the fatty alcohols, generally of natural or synthetic origin, used as starting materials for the synthesis of these compounds.

"Minor proportion" is understood as meaning a maximum cumulative amount of "impurities" of 5% by weight and preferably of 1% by weight, based on the total weight of the above-mentioned alkyl glycosides.

The compositions based on isostearyl glycoside and isostearyl alcohol which are used as agents for improving water resistance within the framework of the present invention can be prepared simply by mixing their constituents in desired predetermined proportions.

On the industrial scale, they will preferably be prepared by one of the two conventional methods used for the synthesis of alkyl polyglycosides and especially by reacting isostearyl alcohol in an acid medium with a saccharide which has an anomeric OH group, such as glucose or dextrose.

Such methods of synthesis are well known and have been widely described in the literature, particularly in documents WO 92/06778, WO 97/02091 or WO 97/18033.

If appropriate, this synthesis may be completed by operations involving neutralization, filtration, partial extraction or distillation of the excess fatty alcohol, or decolorization.

According to one particular characteristic of the invention, the above-mentioned compositions for improving water resistance comprise 10 to 25% by weight of an isostearyl glycoside with a degree of polymerization of between 1 and 10 3, and 90 to 75% by weight of isostearyl alcohol.

Advantageously, these compositions for improving water resistance will be used in an amount of between 0.2 and 10% by weight and preferably of between 0.5 and 5% by weight, based on the total weight of the cosmetic composition.

The cosmetic compositions with improved water resistance which are obtainable within the framework of the present invention can have a variety of forms, particularly the form of water-in-oil, oil-in-water or water-in-oil-in-water emulsions.

These emulsions may be prepared by the conventional methods described in the state of the art, for example by simple dispersion of a fatty phase in a hydrophilic phase in the case of oil-in-water emulsions, or by simple dispersion of a hydrophilic phase in a fatty phase in the case of a water-in-oil emulsion these operations being effected in the presence of an emulsifying system and optionally of a co-emulsifier and/or a stabilizer, it being possible for the dispersion to be prepared cold in view of the liquid nature of the composition based on isostearyl glycoside and isostearyl alcohol which is used as the agent for improving water resistance.

Of course, these emulsions can also comprise one or more compounds selected from humectants, for example glycerol, preservatives, for example the products known under the name SEPICIDE®, colorants, perfumes, cosmetic active ingredients, mineral or organic sun filters, mineral fillers such as iron oxides, titanium oxides and talcum, synthetic fillers such as nylons and micropearls, and plant extracts.

The latter compounds may be introduced into the hydrophilic phase or into the fatty phase, depending on their affinity for these phases, either during the above-mentioned dispersion phase or optionally at a later stage.

As regards the nature of the oils which can be used as the fatty phase, reference may be made to the state of the art and especially the patent documents cited above.

According to a second feature, the present patent application aims to cover a method of improving the water resistance of a cosmetic composition which is essentially characterized in that it consists in incorporating into said cosmetic composition an effective amount of an agent for improving water resistance which is based on isostearyl glycoside and isostearyl alcohol, as defined above.

The invention will be illustrated in greater detail by means of the following Examples, which are given solely by way of illustration.

Unless indicated otherwise, the percentages in these Examples are expressed by weight and the temperature is room temperature.

EXAMPLE 1

Process for the Preparation of a Composition Based on Isostearyl Glycoside and Isostearyl Alcohol Which is Useful as an Agent for Improving the Water Resistance of a Cosmetic Composition Isostearyl alcohol (a product marketed by UNICHEMA under the name PRISORINE® 3515 or by HENKEL under the name SPEZIOL C18 ISO) is introduced into a multipurpose reactor.

Glucose is also introduced into the reactor so that the molar ratio of isostearyl alcohol to glucose is 6/1.

The glucose is then reacted with the fatty alcohol for 6 hours at a temperature of about 100° C., under partial vacuum, in the presence of an acid catalyst.

After the reaction, the catalyst is neutralized with a base.

The composition obtained, which is in the form of a liquid, comprises:

83.9% of isostearyl alcohol, 16.1% of isostearyl glycoside.

EXAMPLE 2

Demonstration of the Properties of the Compositions Based on Isostearyl Glycoside and Isostearyl Alcohol as Agents for Improving the Water Resistance of a Cosmetic Composition The following water resistance evaluation test was performed to demonstrate the remarkable properties of the compositions based on isostearyl glycoside and isostearyl alcohol which are used within the framework of the present invention.

An emulsion film of constant thickness is applied to a glass plate with the aid of a film applicator having a 120 μm aperture.

The color and cover of the film are measured a first time (against a black background) with the aid of an L,a,b system Minolta chromameter after a drying time of 30 minutes.

The glass plate is then immersed for 20 min in water at 25° C. containing a continuous agitation system.

After the film has dried (30 min), the uniformity of the film is scored as follows:

+: if the cover is homogeneous;

−: if blank zones without emulsion are present (complete removal of the emulsion).

Readings are also taken in the L,a,b system.

The values L, a and b (means of 5 experiments) are summed and the percentage of residual film after immersion is calculated according to the following formula:

$$\% \text{ residual film} = \frac{L + a + b \text{ (before immersion)}}{L' + a' + b' \text{ (after immersion)}} \times 100$$

A complementary sensory evaluation was performed by a panel made up of seven experienced persons.

The texture of the emulsions was evaluated by spreading about 0.2 g of emulsion over the back of the hand and using the following assessment criteria:

difficulty of spreading, greasy sensation, sticky effect.

Several types of emulsions were evaluated.

A. OIL-IN-WATER EMULSIONS

The emulsions subjected to these evaluations were prepared by the following procedure:

a) a composition "A" (fatty phase) is heated to about 75° C.;

b) a composition "B" (aqueous phase) is heated to about 75° C.;

c) a composition "C" (pigment) is ground in a ball mill;

e) the ground composition "C" is added to composition "B" at about 75° C.;

f) composition "A" is emulsified at about 75° C. in the composition resulting from the mixture obtained in step e);

g) a composition "D" is added at about 75° C. to the mixture formed in f); and h) as the resulting mixture is cooling, a composition "E" (preservative, perfume) is added at about 40° C.

Six emulsions of the oil-in-water type were prepared by following this experimental procedure.

The qualitative and quantitative compositions of these emulsions are given in Table I below:

Composition D is a composition containing 50% by weight of fatty phase prepared by retaining proportions analogous to formulation A and incorporating 10% of phenyltrimethicone (a product known under the name DC 556, marketed by DOW CORNING).

Composition E is identical to composition A except that the composition based on isostearyl glycoside and isostearyl alcohol has been replaced with a composition of the MONTANOV® 68 type containing a mixture of alkyl polygly-

TABLE I

| COMPOSITON EVALUATED | A | B | C | D | E | F |
|---|---|---|---|---|---|---|
| Phase A | | | | | | |
| Glyceryl stearate/PEG-100 stearate | 6% | 6% | 6% | 6% | 6% | 6% |
| Agent tested | 3% | 0% | 3% | 0% | 3% | 3% |
| Glycol palmitate | 2% | 2% | 2% | 5.5% | 2% | 2% |
| Isononyl isononanoate | 4% | 4% | 4% | 11.5% | 4% | 4% |
| Caprylic/capric triglycerides | 4% | 4% | 4% | 11.5% | 4% | 4% |
| Cyclomethicone | 4% | 4% | 4% | 11.5% | 4% | 4% |
| DC 556 | — | — | — | 10% | — | — |
| Phase B | | | | | | |
| Xanthan gum | 0.15% | 0.15% | 0.15% | 0.15% | 0.15% | 0.15% |
| EDTA | 0.05% | 0.05% | 0.05% | 0.05% | 0.05% | 0.05% |
| Polymethyl methacrylate | 2% | 2% | 2% | 2% | 2% | 2% |
| Water | qsp100% | qsp100% | qsp100% | qsp100% | qsp100% | qsp100% |
| Phase C | | | | | | |
| Butylene glycol | 4% | 4% | 4% | 4% | 4% | 4% |
| PEG 400 | 4% | 4% | 4% | 4% | 4% | 4% |
| Titanium oxide | 7% | 7% | 7% | 7% | 7% | 7% |
| Talcum | 2% | 2% | 2% | 2% | 2% | 2% |
| Yellow iron oxide | 0.8% | 0.8% | 0.8% | 0.8% | 0.8% | 0.8% |
| Red iron oxide | 0.3% | 0.3% | 0.3% | 0.3% | 0.3% | 0.3% |
| Black iron oxide | 0.05% | 0.05% | 0.05% | 0.05% | 0.05% | 0.05% |
| Phase D | | | | | | |
| $C_{13-14}$ isoparaffin/polyacrylamide/laureth-7 | 0.5% | 0.5% | 0.5% | 0.5% | 0.5% | 0.5% |
| Phase E | | | | | | |
| Perfume | qs | qs | qs | qs | qs | qs |
| Preservative | qs | qs | qs | qs | qs | qs |

Composition A was prepared using the composition of Example 1 based on isostearyl glycoside and isostearyl alcohol as the agent for improving water resistance (agent tested).

Compositions B to F were Prepared for Comparison.

Composition B is identical to composition A except that it does not contain any composition based on isostearyl glycoside and isostearyl alcohol.

Composition C is identical to composition A except that the composition of Example 1 has been replaced with an agent for improving water resistance which is recommended in the state of the art, namely the product ANTARON® WP-660 (Tricontanyl PVP).

cosides in which the fatty chains comprise 16 and 18 carbon atoms, and a mixture of fatty alcohols of the same chain length, prepared by following the experimental procedure described in Example 1 of document WO 92/06778.

Composition F is identical to composition A except that the composition based on isostearyl glycoside and isostearyl alcohol has been replaced with a composition containing a mixture of alkyl polyglycosides in which the fatty chains comprise 16 and 18 carbon atoms, and a mixture of fatty alcohols of the same chain length, prepared by following the experimental procedure described in Example 4 of document WO 97/02091.

The results of the evaluation tests performed on these emulsions have been collated in Table II below:

TABLE II

| COMPOSITION | A | B | C | D | E | F |
|---|---|---|---|---|---|---|
| Stability | Stable RT/ 40/50° C. >1 month | Stable RT/ 40/50° C. >1 month | Stable RT/ 40/50° C. >1 month | Exudation of oil at RT, phase separation at 40° C. and 50° C. after 1 month | Stable RT/ 40/50° C. >1 month | Stable RT/ 40/50° C. >1 month |

TABLE II-continued

| COMPOSITION | A | B | C | D | E | F |
|---|---|---|---|---|---|---|
| Sensory evaluation | | | | | | |
| spreading | Very easy | Very easy | Very difficult | Fairly easy | Very easy | Very easy |
| greasiness | Not very greasy | Not very greasy | Very greasy | Very greasy | Not very greasy | Not very greasy |
| stickiness | Not sticky | Not sticky | Very sticky | Very sticky | Not sticky | Not sticky |
| Uniformity of film after immersion | + | − | + | + | − | − |
| % residual film | 60% | Not measurable | 72.6% | 59% | Not measurable | Not measurable |

As shown by the results given in Table II, the composition of Example 1 based on isostearyl glycoside and isostearyl alcohol makes it possible to improve the water resistance of the oil-in-water emulsion prepared, the deposited film retaining 60% of its integrity after immersion, while at the same time preserving very good sensory properties.

It is noted that the emulsions prepared according to the known state of the art, incorporating a vinylic copolymer (Example C) or a substantial amount of fatty phase comprising phenyltrimethicone (composition D), have a good water resistance but degraded sensory properties (greasy and sticky feel).

The results obtained with compositions E and F based on $C_{16}$ and $C_{18}$ alkyl polyglycosides show the specificity of the compositions based on isostearyl glycosides in terms of the desired effect.

Complementary experiments, whose results are not reported here, have shown that the compositions based on isostearyl glycoside and isostearyl alcohol make it possible to improve the water resistance of cosmetic compositions in emulsion form in an amount of 0.2% by weight or more, the sensory properties being maintained up to a use dose of these compositions of about 10% by weight.

B. WATER-IN-OIL EMULSIONS

The emulsions subjected to these evaluations were prepared by the following procedure:

a) a composition "A" (fatty phase) is heated to about 75° C.;

b) a composition "B" (aqueous phase) is heated to about 75° C.;

c) a composition "C" (pigment) is ground in a ball mill;

e) the ground composition "C" is added at about 75° C. to composition "B";

f) the composition resulting from the mixture obtained in step e) is emulsified at about 75° C. in composition "A"; and g) as the resulting mixture is cooling, a composition "D" (preservative, perfume) is added at about 40° C.

4 emulsions of the water-in-oil type were prepared by following this experimental procedure. The qualitative and quantitative compositions of these emulsions of the water-in-oil type are given in Table III below:

TABLE III

| COMPOSITION EVALUATED | A | B | C | D |
|---|---|---|---|---|
| Phase A | | | | |
| MONTANE ® 481 | 6% | 6% | 6% | 6% |

TABLE III-continued

| COMPOSITION EVALUATED | A | B | C | D |
|---|---|---|---|---|
| Agent tested | 3% | 0% | 3% | 0% |
| Paraffin oil | 30% | 30% | 30% | 31.6% |
| Caprylic/capric triglycerides | 4% | 4% | 4% | 4.2% |
| Cyclomethicone | 4% | 4% | 4% | 4.2% |
| DC 556 | — | — | — | 10% |
| Phase B | | | | |
| MgSO₄ | 0.7% | 0.7% | 0.7% | 0.7% |
| Water | qsp 100% | qsp 100% | qsp 100% | qsp 100% |
| Phase C | | | | |
| Butylene glycol | 4% | 4% | 4% | 4% |
| PEG 400 | 4% | 4% | 4% | 4% |
| Titanium oxide | 7% | 7% | 7% | 7% |
| Talcum | 2% | 2% | 2% | 2% |
| Yellow iron oxide | 0.8% | 0.8% | 0.8% | 0.8% |
| Red iron oxide | 0.3% | 0.3% | 0.3% | 0.3% |
| Black iron oxide | 0.05% | 0.05% | 0.05% | 0.05% |
| Phase D | | | | |
| Perfume | qs | qs | qs | qs |
| Preservative | qs | qs | qs | qs |

Composition A was prepared using the composition of Example 1 based on isostearyl glycoside and isostearyl alcohol as the agent for improving water resistance (agent tested).

Compositions B to D were Prepared for Comparison.

Composition B is identical to composition A except that it does not contain any composition based on isostearyl glycoside and isostearyl alcohol.

Composition C is identical to composition A except that the composition of Example 1 has been replaced with an agent for improving water resistance which is recommended in the state of the art, namely the product ANTARON® WP-660 (Tricontanyl PVP).

Composition D is a composition containing 50% by weight of fatty phase prepared by retaining proportions analogous to formulation A and incorporating 10% of phenyltrimethicone (a product known under the name DC 556, marketed by DOW CORNING).

The results of the evaluation tests performed on these emulsions have been collated in Table IV below:

TABLE IV

| COMPOSITION | A | B | C | D |
|---|---|---|---|---|
| Stability | Stable RT/ 40/50° C. >1 month | Stable RT/ 40/50° C. >1 month | Stable RT/ 40/50° C. >1 month | Exudation of oil at RT, phase separation at 40° C. and |

TABLE IV-continued

| COMPOSITION | A | B | C | D |
|---|---|---|---|---|
| | | | | 50° C. after 1 month |
| Sensory evaluation | | | | |
| spreading | Easy | Very difficult | Very difficult | Very difficult |
| greasiness | Very greasy | Very greasy | Very greasy | Very greasy |
| stickiness | Very sticky | Sticky | Very sticky | Very sticky |
| Uniformity of film after immersion | + | + | + | + |
| % residual film | 91% | 80% | 88% | 86% |

As shown by the results given in Table IV, the composition of Example 1 based on isostearyl glycoside and isostearyl alcohol makes it possible to improve the water resistance of the water-in-oil emulsion prepared, the deposited film retaining 91% of its integrity after immersion.

Also, the emulsion obtained with the composition of Example 1 spreads with remarkable ease, in contrast to the other emulsions prepared according to the known state of the art.

It is noted in particular that the emulsions prepared according to the known state of the art, incorporating a vinylic copolymer (Example C) or a substantial amount of fatty phase comprising phenyltrimethicone (composition D), have a good water resistance but are very difficult to spread.

Complementary experiments, whose results are not reported here, have shown that the compositions based on isostearyl glycoside and isostearyl alcohol make it possible to improve the water resistance of cosmetic compositions in emulsion form in an amount of 0.2% by weight or more, the sensory properties being maintained up to a use dose of these compositions of about 10% by weight.

EXAMPLES OF COSMETIC COMPOSITIONS WITH IMPROVED WATER RESISTANCE, OBTAINED ACCORDING TO THE INVENTION

A. OIL-IN-WATER EMULSION

This emulsion was prepared by the following procedure:

a) a composition "A" (fatty phase) containing a composition based on isostearyl glycoside and isostearyl alcohol (product of Example 1) is heated to 70°–75° C.;

b) a composition "B" (aqueous phase) is heated to 70–75° C.;

c) an oil-in-water emulsion is formed by dispersing the fatty phase "A" in the aqueous phase "B" by means of a SILVERSON agitator for 4 min at 4000 rpm;

d) the emulsion is cooled while being stirred with an anchor stirrer; and e) during cooling, a composition "C" (preservative) is added at about 60° C. and a composition "D" (perfume) at about 30° C.

SUN CREAM

A

| Composition of Example 1 | 3% |
|---|---|
| SIMULSOL ® 165 | 6% |
| PECOSIL ® PS100 | 2% |

-continued

SUN CREAM

| $C_{12}$—$C_{15}$ alkyl benzoate | 10% |
|---|---|
| Triglyceride 5545 | 8% |
| Micronized titanium oxide with coating | 10% |
| 3-Benzophenone | 5% |
| Octocrylene | 5% |
| Glycerol | 4% |

B

| Water | qsp 100% |
|---|---|
| SEPICALM ® S | 2% |

C

| SIMULGEL ® A | 1% |
|---|---|
| Cyclomethicone | 5% |
| SEPICIDE ® HB | 1% |

D

| Perfume | 0.2% |
|---|---|

B. WATER-IN-OIL EMULSIONS

SUN CREAM

This emulsion was prepared by the following procedure:

a) a composition "A" (fatty phase) containing a composition based on isostearyl glycoside and isostearyl alcohol (product of Example 1) is heated to 70°–75° C.;

b) a composition "B" (aqueous phase) is heated to 70–75° C.;

c) a water-in-oil emulsion is formed by dispersing the aqueous phase "B" in the fatty phase "A" by means of a SILVERSON agitator for 4 min at 4000 rpm;

d) the emulsion is cooled while being stirred with an anchor stirrer; and e) during cooling, a composition "C" (preservative, perfume) is added at about 30° C.

A

| Composition of Example 1 | 8% |
|---|---|
| Squalane | 30% |
| ELFACOS ® ST9 | 1% |
| Hydrophobic silica | 1% |
| Micronized titanium oxide with coating | 4% |
| Micronized zinc oxide with coating | 2% |
| 3-Benzophenone | 3% |
| Octyl methoxycinnamate | 6% |

B

| Water | qsp 100% |
|---|---|
| Glycerol | 4% |
| $MgSO_4$ | 0.7% |

C

| SEPICIDE ® HB | 1% |
|---|---|
| Perfume | 0.2% |

MASCARA

This emulsion was prepared by following steps a) to d) of the procedure described above for the sun cream, the heating temperature being about 85° C. and the aqueous phase having been ground prior to heating.

A

| Composition of Example 1 | 10% |
|---|---|
| Ozokerite | 10% |

| -continued | |
|---|---|
| Beeswax | 8% |
| Paraffin oil | 5% |
| B | |
| Water | qsp 100% |
| PVP | 0.2% |
| Propylene glycol | 7% |
| Black iron oxide | 6% |
| MgSO$_4$ | 0.7% |
| SEPICIDE ® HB | 1% |

BABY CREAM

This cream soothes diaper rash (protects the skin from irritation associated with the dampness of the diaper and the alkalinity of the urine).

This emulsion was prepared by following the procedure described above for the mascara formulation, the heating temperature being 80° C. and the dispersion being produced under high shear.

| A | |
|---|---|
| Composition of Example 1 | 5% |
| MONTANE ® 80 | 4% |
| Beeswax | 5% |
| Paraffin oil | 20% |
| Squalane | 8% |
| SEPICALM ® VG | 2% |
| Zinc oxide (non-micronized) | 15% |
| MICROPEARL ® M310 | 2% |
| B | |
| Water | qsp 100% |
| Glycerol | 5% |
| MgSO$_4$ | 0.7% |
| SEPICIDE HB | 1% |

C. WATER-IN-OIL-IN-WATER EMULSION MOISTURIZING COMPOSITION

This multiple emulsion was prepared by the following procedure:

a) a composition "A" (fatty phase) containing a composition based on isostearyl glycoside and isostearyl alcohol (product of Example 1) is heated to about 80° C.;

b) a composition "B" (aqueous phase) is heated to 80° C.;

c) a water-in-oil emulsion is formed by dispersing the aqueous phase "B" in the fatty phase "A" by means of a SILVERSON agitator for 4 min at 4000 rpm;

d) the emulsion is cooled while being stirred with an anchor stirrer; and e) during cooling, a composition "C" (stabilizer) is added at about 70° C. and a composition "D" (preservative, perfume) at about 30° C.

| A | |
|---|---|
| Composition of Example 1 | 1% |
| MONTANOV ® 202 | 4% |
| Isononyl isononanoate | 20% |
| SEPILIFT ® DPHP | 1% |
| B | |
| Water | qsp 100% |

| -continued | |
|---|---|
| C | |
| SIMULGEL ® EG | 0.5% |
| D | |
| SEPICIDE ® HB | 0.3% |
| SEPICIDE ® CI | 0.2% |
| Perfume | 0.2% |

What is claimed is:

1. A method of improving the water resistance of a cosmetic composition, which consists in adding to said cosmetic composition an effective amount of a water resistance improving agent comprising:
    10 to 90% by weight of an isostearyl glycoside with a degree of polymerization of between 1 and 3; and
    90 to 10% by weight of isostearyl alcohol.

2. A method according to claim 1, wherein said water resistance improving agent comprises:
    10 to 50% by weight of an isostearyl glycoside with a degree of polymerization of between 1 and 3; and
    90 to 50% by weight of isostearl alcohol.

3. A method according to claim 1, wherein said water resistance improving agent comprises:
    10 to 40% by weight of an isostearyl glycoside with a degree of polymerization of between 1 and 3; and
    90 to 60% by weight of isostearyl alcohol.

4. A method according to claim 1, wherein said water resistance improving agent comprises:
    10 to 25% by weight of an isostearyl glycoside with a degree of polymerization of between 1 and 3; and
    90 to 75% by weight of isostearyl alcohol.

5. A method according to claim 1, wherein said effective amount of water resistance improving agent is between 0.2 and 10% by weight, based on the total weight of the cosmetic composition.

6. A method according to claim 1, wherein said effective amount of water resistance improving agent is between 0.5 and 5% by weight, based on the total weight of the cosmetic composition.

7. A method according to claim 2, wherein said effective amount of water resistance improving agent is between 0.2 and 10% by weight, based on the total weight of the cosmetic composition.

8. A method according to claim 2, wherein said effective amount of water resistance improving agent is between 0.5 and 5% by weight, based on the total weight of the cosmetic composition.

9. A method according to claim 3, wherein said effective amount of water resistance improving agent is between 0.2 and 10% by weight, based on the total weight of the cosmetic composition.

10. A method according to claim 3, wherein said effective amount of water resistance improving agent is between 0.5 and 5% by weight, based on the total weight of the cosmetic composition.

11. A method according to claim 4, wherein said effective amount of water resistance improving agent is between 0.2 and 10% by weight, based on the total weight of the cosmetic composition.

12. A method according to claim 4, wherein said effective amount of water resistance improving agent is between 0.5 and 5% by weight, based on the total weight of the cosmetic composition.

13. A method according to claim 1, wherein said cosmetic composition is in a form selected from the group consisting of a water-in-oil emulsion, an oil-in-water emulsion and a water-in-oil-in-water emulsion.

\* \* \* \* \*

UNITED STATES PATENT AND TRADEMARK OFFICE
CERTIFICATE OF CORRECTION

PATENT NO. : 6,464,993 B1 Page 1 of 1
DATED : October 15, 2002
INVENTOR(S) : Milius et al.

It is certified that error appears in the above-identified patent and that said Letters Patent is hereby corrected as shown below:

<u>Title page, Item [54], and Column 1, line 1,</u>
Please delete "BASES" and insert -- BASED --.

<u>Title page,</u>
Item [75], please delete inventor last name "Branco" and insert -- Brancq --;
Please delete inventor last name "Almaric" and insert -- Amalric --.

Signed and Sealed this

Ninth Day of September, 2003

JAMES E. ROGAN
*Director of the United States Patent and Trademark Office*